United States Patent [19]

Sekigawa et al.

[11] Patent Number: 5,217,720
[45] Date of Patent: Jun. 8, 1993

[54] COATED SOLID MEDICAMENT FORM HAVING RELEASABILITY IN LARGE INTESTINE

[75] Inventors: Fujio Sekigawa, Saitama; Yoshiro Onda, Tokyo, both of Japan

[73] Assignee: Shin-Etsu Chemical Co., Ltd., Tokyo, Japan

[21] Appl. No.: 726,587

[22] Filed: Jul. 8, 1991

[30] Foreign Application Priority Data

Jul. 10, 1990 [JP] Japan ................... 2-182157

[51] Int. Cl.⁵ ............................... A61K 9/36
[52] U.S. Cl. .................... 424/480; 424/458; 424/461; 424/479; 424/482; 424/493; 424/494; 514/960; 514/887
[58] Field of Search ............... 536/20; 514/55; 424/480, 479, 482, 461, 458, 493, 494, 471, 472

[56] References Cited

U.S. PATENT DOCUMENTS 4,432,966 2/1984 Zeitoun et al. ................... 424/471
4,876,097 10/1989 Autant et al. ..................... 424/438

*Primary Examiner*—Thurman K. Page
*Assistant Examiner*—James M. Spear
*Attorney, Agent, or Firm*—McAulay Fisher Nissen Goldberg & Kiel

[57] ABSTRACT

A coated solid medicament form suitable for oral administration having reliable releasability of the active ingredient only in the large intestine is proposed. The medicament form is prepared by coating a core solid medicament form containing the active ingredient first with a chitosan having a specific degree of deacetylation and a specific degree of polymerization and then top-coated with a specific enteric-soluble polymer which is a hydroxypropyl methyl cellulose acetate succinate or a hydroxypropyl methyl cellulose hexahydrophthalate. The releasability of the active ingredient only in the large intestine can be more reliable when the core medicament form is, prior to coating with chitosan, provided with an enteric undercoating layer.

10 Claims, No Drawings

COATED SOLID MEDICAMENT FORM HAVING RELEASABILITY IN LARGE INTESTINE

BACKGROUND OF THE INVENTION

The present invention relates to a coated solid medicament form having releasability of the active ingredient only in the large intestine or, more particularly, to a coated solid medicament form which, when orally administrated, passes unaffected through the stomach and small intestine but is disintegrated when it reaches the large intestine so as to release the therapeutically active ingredient contained therein only in the large intestine.

It is eagerly desired in recent years to develop a solid medicament form capable of releasing the active ingredient only in the large intestine when it is orally administrated in view of the increasing trend of various diseases of the large intestine such as ulcerative colitis and the like, for which diseases oral administration of a medicament can be an efficient therapeutic means, and in view of the fact that certain medicinal compounds such as insulin used for the therapeutic treatment of diabetes, which hitherto cannot be orally administrated due to decomposition and deactivation by digestive enzymes such as peptidase in the digestive organ, should desirably be rendered adaptable to oral administration.

With an object mentioned above, a proposal is made in "Fine Chemicals", Nov. 1, 1989 issue, to prepare a coated solid medicament form by using a specific polyurethane degradable in the large intestine. In this coated solid medicament form, the biodegradability of the specific polyurethane is utilized under the influences of the bacteria inhabiting in the large intestine to cause disintegration of the solid medicament form in the large intestine. An important problem here is, since polyurethane is a totally synthetic substance, to ensure that absolutely no adverse effect such as toxicity is exhibited against the human body by the product produced by the decomposition of the polyurethane in the large intestine.

Standing on a guide principle that the above mentioned problem due to the decomposition product of the coating material produced in the large intestine could be mostly solved by using a coating material of natural origin, the inventors have conducted extensive investigations to develop a novel coating on a solid medicament form by utilizing a coating material of natural origin, optionally, in combination with another coating material, which may not be of a natural origin, hardly decomposable in the digestive canals to be freed from the problem of toxicity or any adverse influences against human health.

SUMMARY OF THE INVENTION

The present invention accordingly has an object to provide a novel coated solid medicament form which is stable in the stomach and in the small intestine but can be readily disintegrated in the large intestine to release the pharmaceutically effective ingredient contained therein without producing any decomposition product having toxicity against human body.

Thus, the coated solid medicament form of the present invention having releasability of the active ingredient only in the large intestine comprises, in the first embodiment:

(a) a core medicament form containing an active ingredient;

(b) a first coating layer formed from chitosan on the core medicament form, the coating amount thereof being in the range from 2 to 20% by weight based on the core medicament form; and (c) a second coating layer made from a first enteric coating material, which is preferably a hydroxypropyl methyl cellulose acetate succinate or a hydroxypropyl methyl cellulose hexahydrophthalate, on the first coating layer, the coating amount thereof being in the range from 3 to 30% by weight based on the core medicament form.

Further, the coated solid medicament form of the present invention having releasability of the active ingredient only in the large intestine comprises, in the second embodiment:

(a) a core medicament form containing an active ingredient;

(d) an undercoating layer formed from a second enteric coating material on the core medicament, the coating amount thereof being in the range from 3 to 30% by weight based on the core medicament form;

(b) a first coating layer formed from chitosan on the undercoating layer, the coating amount thereof being in the range from 2 to 20% by weight based on the core medicament form; and (c) a second coating layer made from a first enteric coating material, on the first coating layer, the coating amount thereof being in the range from 3 to 30% by weight based on the core medicament form.

The chitosan forming the first coating layer preferably has a degree of deacetylation of at least 85% and such a degree of polymerization that a 0.5% by weight solution thereof in a 0.5% by weight aqueous solution of acetic acid has a viscosity of at least 30 centistokes at 20° C.

Further, the cellulose ethers forming the second coating layer exhibits such a solubility behavior that a film prepared therefrom to have specified dimensions is stable in the first fluid specified for the disintegration test according to Japanese Pharmacopoeia and cannot be dissolved at least for 120 minutes at 37° C. in a Clark-Lubs' buffer solution having a pH of 6.5 or higher.

DETAILED DESCRIPTION OF THE PREFERRED EMBODIMENTS

As is described above, the coated solid medicament form of the present invention comprises two or three successive coating layers each formed from a specified coating material, of which the topmost coating layer, i.e. the second coating layer mentioned above, is formed from a cellulose ether such as hydroxypropyl methyl cellulose acetate succinate and hydroxypropyl methyl cellulose hexahydrophthalate and the layer below the topmost coating layer, i.e. the first coating layer mentioned above, is formed from chitosan.

Chitosan is a nitrogen-containing polymeric material obtained by a chemical treatment of chitin, which is a natural polymer found in the crust of various crustacean animals such as crabs and lobsters. Though insoluble in neutral water, chitosan is dissolved in a dilute aqueous solution of an organic or inorganic acid since the amino groups —$NH_2$ in the molecular structure thereof are converted into an ammonium salt in an acidic aqueous solution. Therefore, a film of chitosan is dissolved when it is in the gastric juice having acidity but cannot be dissolved in the intestinal juice having a much higher pH value than the gastric juice.

On the other hand, it is reported that, when various kinds of animals are fed with chitosan, it is digested to a considerable extent in their digestive canals although the exact site where digestion of chitosan takes place is not well known. This is in the same line as many of dietary fibers which are digestible in the digestive organs of animals since chitosan is also a kind of dietary fibers.

The above described facts led the inventor to obtain an idea that, when a core medicament form containing an active ingredient is first coated with chitosan and then overcoated with an enteric coating material, the thus double-coated solid medicament form would be stable and unaffected in the acidic environment of the stomach as being protected by the enteric top coating layer and also prevented from disintegration in the small intestine, where the enteric top coating layer is dissolved away, by virtue of the coating layer of chitosan resistant against the alkaline environment in the small intestine while the coating layer of chitosan is decomposed in the large intestine due to the biodegradability of chitosan by the bacteria abundantly inhabiting in the large intestine to release the active ingredient contained in the core solid medicament form.

As is mentioned before, chitosan is soluble in a diluted aqueous solution of an organic or inorganic acid or in a mixture of water and ethyl alcohol so that a coating solution of chitosan can readily be prepared by dissolving chitosan in these liquids in a concentration suitable for coating of the core solid medicament form. Once a coating film of chitosan is formed on the core medicament form, the coating film is stable in an aqueous solution of a high pH value but can be readily dissolved in an aqueous solution having a pH lower than a critical value which depends on the chemical composition of the chitosan to some extent.

It is known that the intestinal juice in the human small intestine is weakly alkaline and has a pH close to 6.8 which is the pH of the second fluid specified in Japanese Pharmacopoeia for the disintegration test of enteric-coated preparations. Namely, the enteric coating films on a solid medicament form are usually formulated so as to be resistant against an acidic aqueous solution but to be dissolvable in the above mentioned second fluid or a more alkaline aqueous solution. In many cases, the enteric coating films are formulated so as to be dissolved in an aqueous solution buffered to have a pH of 5 to 6 because, in most cases, it is desirable that the active ingredient in the enteric-coated solid medicament form is released in the upper part of the small intestine. Chitosan is usually also dissolved or, at least, greatly swollen in an aqueous solution having such a pH value.

It is therefore very important that the chemical compositions of the chitosan for the first coating layer and the enteric coating material for the second coating layer are adequately selected in order to ensure that the double-coated solid medicament form is safe from disintegration in the small intestine even after dissolution of the topmost enteric coating layer to be transferred into the large intestine.

The results of the detailed experimentation undertaken in this regard specify that the chitosan used for the first coating layer should have a degree of deacetylation of at least 85% and have such a degree of polymerization that a 0.5% by weight solution thereof in a 0.5% aqueous solution of acetic acid has a viscosity of at least 30 centistokes at 20° C. When the values of either one or both of these parameters are lower than the above mentioned respective lower limits, the critical pH value for the solubility behavior of the chitosan would be too high so that eventual dissolution of the coating layer of chitosan may take place already in the small intestine where the pH value is somewhat lower than the critical pH value for the dissolution of chitosan.

A coating solution for forming a coating layer of chitosan on the core solid medicament form can be prepared by dissolving the above specified chitosan in a mixture of water and ethyl alcohol or an aqueous medium containing acetic or hydrochloric acid in an amount required for dissolving the chitosan. The concentration of chitosan in the thus prepared coating solution is in the range from 0.2 to 5% by weight. A higher concentration of chitosan than above is undesirable because of the difficulties caused in the spraying work of the coating solution due to the unduly high viscosity of the solution. The coating amount of chitosan is usually in the range from 2 to 20% by weight based on the core solid medicament form. The coating amount should be sufficient to ensure stability of the double-coated solid medicament form of the invention for at least 120 minutes when it is subjected to a disintegration test for enteric-coated preparations according to the procedure specified in Japanese Pharmacopoeia by using Clark-Lubs' buffer solution having a pH value of 6.5 or higher.

The requirements for the enteric coating material forming the topmost coating layer on the double-coated solid medicament form of the invention are also somewhat different from those used in conventional enteric-coated solid medicament forms. The conclusion obtained in a detailed experimentation is that the enteric coating material should be stable in the first fluid for the disintegration test specified in Japanese Pharmacopoeia and resistant for at least 120 minutes at 37° C. against the test by using a Clark-Lubs' buffer solution having a pH of 6.5 or lower while soluble within 60 minutes in a Clark-Lubs' buffer solution having a pH of 8.0. When the double-coated solid medicament form is prepared by using an enteric coating material which is persistent for more than 60 minutes in the above mentioned test with a Clark-Lubs' buffer solution of pH 8.0, the coated solid medicament form would no longer be disintegrable not only in the small intestine but also when it reaches the large intestine.

The above mentioned test for the solubility behavior of the enteric coating material refers to a procedure in which a film of the material having a thickness of 90 to 110 $\mu$m is prepared by casting from a solution of the material in a suitable solvent and a 10 mm by 10 mm square test specimen of the film is subjected to a test according to the procedure specified in Japanese Pharmacopoeia for the disintegration test of enteric-coated preparations, "(i) Preparations other than granules and capsules filled with beads".

In short, the enteric coating material for the topmost coating layer of the inventive double-coated solid medicament form is required to have a critical pH value, above which dissolution of the coating film takes place, should be as high as possible in order that the topmost enteric coating layer is dissolved in the as lower as possible part of the small intestine to ensure reliable transfer of the medicament form into the large intestine without causing any changes in the coating layer of chitosan and release of the active ingredient therefrom.

The inventors have conducted extensive studies to find an enteric coating material to satisfy the above mentioned requirements leading to a conclusion that suitable materials include hydroxypropyl methyl cellulose acetate succinate and hydroxypropyl methyl cellulose hexahydrophthalate. The coating method using these cellulose derivatives as the coating material can be conventional. For example, the cellulose derivative is dissolved in ethyl alcohol or in a mixture of ethyl alcohol and water to prepare a coating solution or a fine powder of the cellulose derivative is dispersed in water to prepare a coating dispersion and the core solid medicament form provided with the first coating layer of chitosan is coated by spraying the thus prepared coating solution or dispersion in a suitable coating machine such as pan coaters and fluidized-bed coaters. The coating amount of this second coating layer is usually in the range from 3 to 30% by weight based on the uncoated core solid medicament form in order to ensure reliable stability of the coated medicament form against gastric juice.

The double-coated solid medicament form described above was found quite satisfactory to ensure release of the active ingredient only in the large intestine in most cases excepting for several cases in which a slight release of the active ingredient from the orally administrated medicament form begins already in the small intestine after dissolution of the topmost enteric coating layer due to swelling of the layer of chitosan and permeation of the active ingredient through the thus swollen chitosan layer depending on various conditions such as an extremely high solubility behavior of the active ingredient.

The above mentioned premature release of the active ingredient in the small intestine can be effectively prevented by providing the core medicament form with an undercoating layer of an enteric material before coating with chitosan thus to prepare a triple-coated solid medicament form. The enteric coating material can be any of conventional ones including, for example, hydroxypropyl methyl cellulose phthalate, hydroxypropyl methyl cellulose acetate succinate, hydroxypropyl methyl cellulose hexahydrophthalate, cellulose acetate phthalate, carboxymethyl ethyl cellulose, methacrylic acid copolymers in the form of a solid or emulsion and the like. The coating method by using these coating materials can also be conventional to form a coating layer on the core solid medicament form such as beads and tablets. The coating amount for this enteric undercoating should be sufficient to pass the disintegration test for enteric-coated preparations specified in Japanese Pharmacopoeia or, in particular, in the range from 3 to 30% by weight based on the core solid medicament form before coating calculated as solid. When adequately provided with such an enteric undercoating layer, the triple-coated solid medicament form of the invention is efficiently prevented from the troubles of premature release of the active ingredient or swelling of the form as a whole in the small intestine even after dissolution of the topmost enteric coating layer followed by swelling of the coating layer of chitosan.

It is of course optional according to need in the preparation of the double- or triple-coated solid medicament form of the invention to provide other different coating layers such as a non-enteric film coating layer on the core medicament form using hydroxypropyl cellulose or hydroxypropyl methyl cellulose, an over coating layer on the enteric second coating layer and an intermediate coating layer or layers between the enteric undercoating layer and the first coating layer of chitosan and/or between the first coating layer of chitosan and the enteric second coating layer. It is further optional that a capsuled medicament form is prepared by filling a hard capsule made from gelatin or other water-soluble or enteric polymeric material with the double- or triple-coated solid medicament form of the invention.

In the following, particular embodiments of the present invention are described in more detail by way of examples, which, however, should never be construed to limit the scope of the invention in any way. The terms of "%" and "parts" in the following always refer to "% by weight" excepting for the degree of deacetylation of chitosan and "parts by weight", respectively.

EXAMPLE 1

Tablets each having a diameter of 8 mm and weighing 200 mg were prepared from a blend of 99 parts of lactose, 1 part of magnesium stearate and 100 parts of salicylamide as a simulate active ingredient. The tablets were coated with a hydroxypropyl methyl cellulose phthalate according to Japanese Pharmacopoeia 200731 (HP-55, a product by Shin-Etsu Chemical Co.) in a coating amount of 20 mg per tablet. These coated tablets could pass the disintegration test of enteric medicament forms according to the procedure specified in Japanese Pharmacopoeia.

The enteric-coated tablets above obtained were then coated with chitosan in a coating amount of 10 mg per tablet by using a 0.5% solution of a chitosan, of which the degree of deacetylation was 98% and a 0.5% solution in a 0.5% aqueous solution of acetic acid had a viscosity of 620 centistokes at 20° C., in a 0.3% aqueous solution of acetic acid.

Finally, the above obtained twice-coated tablets were finishcoated in a coating amount of 20 mg per tablet as dried by using a coating solution prepared by dissolving 5 parts of a hydroxypropyl methyl cellulose hexahydrophthalate, of which the contents of the methoxyl groups, hydroxypropoxyl groups and hexahydrophthalyl groups were 17.3%, 6.1% and 38.1%, respectively, and 0.25 part of triethyl citrate in 94.75 parts of anhydrous ethyl alcohol.

The triple-coated tablets prepared in the above described manner were subjected to the disintegration test of enteric medicament forms by using the first fluid according to Japanese Pharmacopoeia to find no changes in the tablets after standing for 120 minutes. The tablets were then subjected to the disintegration test according to the testing procedure with the second fluid specified in Japanese Pharmacopoeia but replacing the second fluid with a Clark-Lubs' buffer solution having a pH of 7.5 to find dissolution of the topmost enteric coating layer of hydroxypropyl methyl cellulose hexahydrophthalate taking place within 120 minutes without noticeable changes in the form of the medicament form per se.

In the next place, the coated tablets after removal of the topmost enteric coating layer were subjected to an in vitro biodegradability test of the chitosan layer. Thus, a 1 g portion of a fresh human feces was taken with minimum exposure to the atmospheric air and added to a GAM semi-fluid stab culture medium to make up a total amount of 10 g followed by 10 times dilution thereof to prepare a bacterial mother liquor. A portion of this mother liquor was introduced into a hermetically sealable vessel together with an about 200 times amount of the fresh culture medium and, after replacement of the air inside with nitrogen, cultured anaerobically at 37° C. for 24 hours to prepare a human fecal culture medium. Six of the tablets under testing were transferred into 100 ml of the fecal culture medium which was agitated at 37° C. by using a magnetic stirrer under an atmosphere of nitrogen to find disintegration of the tablets within 70 to 130 minutes supporting the conclusion that the coated solid medicament form could release the active ingredient therein only in the large intestine.

Separately from the above, a film of the hydroxypropyl methyl cellulose hexahydrophthalate used above having a thickness of 90 to 110 μm was prepared by casting a 5% solution thereof in ethyl alcohol and a 10 mm by 10 mm wide piece of the film was subjected to the disintegration test of Japanese Pharmacopoeia for (i) enteric-coated preparations other than granules and capsules filled with beads. The results were that no noticeable changes were found in the appearance of the film in the first fluid and, in the test using Clark-Lubs' buffer solutions, no noticeable changes were found within 120 minutes when the pH of the solution was 6.5 while the film was dissolved within 25 to 27 minutes when the solution had a pH of 8.0.

EXAMPLE 2

The simulate tablets after coating with the hydroxypropyl methyl cellulose phthalate HP-55 prepared in Example 1 were coated in a coating amount of 10 mg per tablet with one of five grades of chitosans I to V having different degrees of deacetylation and different viscosities of a 0.5% solution thereof in a 0.5% aqueous solution of acetic acid at 20° C. specified below.

Chitosan I: degree of deacetylation 98%; solution viscosity 620 centipoise
Chitosan II: degree of deacetylation 96%; solution viscosity 120 centipoise
Chitosan III: degree of deacetylation 94%; solution viscosity 21 centipoise
Chitosan IV: degree of deacetylation 82%; solution viscosity 240 centipoise
Chitosan V: degree of deacetylation 75%; solution viscosity 130 centipoise The thus double-coated tablets were subjected, without providing the topmost enteric coating layer, to the disintegration test using the second fluid specified in Japanese Pharmacopoeia to find that no noticeable changes were found in the tablets coated with the chitosan I or II within 120 minutes while disintegration took place within 120 minutes in the tablets coated with the chitosan III, IV or V.

EXAMPLE 3

Triple-coated tablets were prepared in the same manner as in Example 1 excepting replacement of the hydroxypropyl methyl cellulose hexahydrophthalate for the topmost enteric coating layer with a hydroxypropyl methyl cellulose acetate succinate, referred to as HPMCAS hereinbelow (AS-HG, a product by Shin-Etsu Chemical Co.), or a hydroxypropyl methyl cellulose phthalate, referred to as HPMCP hereinbelow (HP-55, a product by Shin-Etsu Chemical Co.). Coating with these cellulose derivatives was performed by using a 8% solution thereof in a 8:2 by weight mixture of ethyl alcohol and water.

These coated tablets were subjected to the disintegration test according to Japanese Pharmacopoeia. The results were that the HPMCAS-coated tablets were unchanged but the HPMCP-coated tablets were disintegrated within 32 to 36 minutes in the first fluid. The results of the solubility test using film specimens of the coating materials in Clark-Lubs' buffer solutions of different pH values were that the film of HPMCAS was undissolved after 120 minutes in the solution of pH 6.5 but was dissolved within 10 to 12 minutes in the solution of pH 8.0 while the film of HPMCP was dissolved within 9 to 13 minutes in the solution of pH 6.5 and within 5 to 9 minutes in the solution of pH 8.0.

EXAMPLE 4

A blend of 60% salicylamide and 40% lactose was granulated into beads by extrusion through a screen having openings of 0.6 mm diameter. The beads were first coated with the same hydroxypropyl methyl cellulose phthalate as used in Example 1 in a coating amount of 20% followed by coating with the same chitosan as used in Example 1 in a coating amount of 10% as solid based on the uncoated beads by using a 0.4% solution thereof in a 0.25% aqueous solution of acetic acid. Finally, the beads were coated with the same hydroxypropyl methyl cellulose hexahydrophthalate as used in Example 1 in a coating amount of 20% as solid based on the uncoated beads by using a solution prepared by dissolving 4 parts of the cellulose derivative and 0.2 part of triethyl citrate in 95.8 parts of anhydrous ethyl alcohol.

The thus triple-coated beads were subjected to the disintegration test of enteric medicament forms according to Japanese Pharmacopoeia to find no noticeable changes within 120 minutes in the first fluid while, in the succeeding test performed by using a Clark-Lubs' buffer solution having a pH of 7.5 in place of the second fluid, the topmost enteric coating layer had been dissolved away after 120 minutes but without noticeable changes in the shape of the respective beads.

What is claimed is:

1. A coated solid medicament form having releasability of the active ingredient only in the large intestine which comprises:
   (a) a core medicament form containing salicylamide as a therapeutically active ingredient;
   (b) a first coating layer formed from chitosan on the core medicament form, the coating amount thereof being in the range from 2 to 20% by weight based on the core medicament form; and
   (c) a second coating layer made from a first enteric coating material, which is a hydroxypropyl methyl cellulose acetate succinate or a hydroxypropyl methyl cellulose hexahydrophthalate, on the first coating layer, the coating amount thereof being in the range from 3 to 30% by weight based on the core medicament form.

2. A coated solid medicament form having releasability of the active ingredient only in the large intestine which comprises:
   (a) a core medicament form containing salicylamide as a therapeutically active ingredient;
   (d) an undercoating layer formed from a second enteric coating material on the core medicament, the coating amount thereof being in the range from 3 to 30% by weight based on the core medicament form;
   (b) a first coating layer formed from chitosan on the undercoating layer, the coating amount thereof being in the range from 2 to 20% by weight based on the core medicament form; and (c) a second coating layer made from a first enteric coating material, which is a hydroxypropyl methyl cellulose acetate succinate or a hydroxypropyl methyl cellulose hexahydrophthalate, on the first coating layer, the coating amount thereof being in the range from 3 to 30% by weight based on the core medicament form.

3. The coated solid medicament form having releasability of the salicylamide only in the large intestine as claimed in claim 1, in which the chitosan forming the first coating layer has a degree of deacetylation of at least 85% and such a degree of polymerization that a 0.5% by weight solution thereof in a 0.5% by weight aqueous solution of acetic acid has a viscosity of at least 30 centistokes at 20° C.

4. The coated solid medicament form having releasability of the salicylamide only in the large intestine as claimed in claim 2, in which the chitosan forming the first coatining layer has a degree of deacetylation of at least 85% and such a degree of polymerization that a 0.5% by weight solution thereof in a 0.5% by weight aqueous solution of acetic acid has a viscosity of at least 30 centistokes at 20° C.

5. The coated solid medicament form having releasability of the salicylamide only in the large intestine as claimed in claim 2, in which the second enteric coating material is selected from the group consisting of hydroxypropyl methyl cellulose phthalate, hydroxypropyl methyl cellulose acetate succinate, hydroxypropyl methyl cellulose hexahydrophthalate, cellulose acetate phthalate, carboxymethyl ethyl cellulose and methacrylic acid copolymers.

6. A method for the preparation of a coated solid medicament form which releases the active ingredient in the large intestine comprising the steps of:
   a) coating a solid medicament containing salicylamide as a core with a layer of chitosan in a coating amount in the range from 2 to 20% by weight based on the weight of the core medicament form; and b) coating the chitosan-coated form from step a with a first enteric coating layer of hydroxypropyl methyl cellulose acetate succinate or hydroxypropyl methyl cellulose hexahydrophthalate in a coating amount in the range from 3 to 30% by weight based on the weight of the core medicament form.

7. The method of claim 6 wherein prior to step a, the core medicament form is coated with an enteric coating material in an amount from about 3 to 30% by weight based on the weight of the core medicament form.

8. The method of claim 6 wherein the chitosan has a degree of deacetylation of at least 85% and a degree of polymerization such that a 0.5% by weight solution thereof in a 0.5% by weight aqueous solution of acetic acid has a viscosity of at least 30 centistokes at 20° C.

9. The method of claim 7 wherein the chitosan has a degree of deacetylation of at least 85% and a degree of polymerization such that a 0.5% by weight solution thereof in a 0.5% by weight aqueous solution of acetic acid has a viscosity of at least 30 centistokes at 20° C.

10. The method of claim 7 wherein the enteric coating material is selected from the group consisting of hydroxypropyl methyl cellulose phthalate, hydroxypropyl methyl cellulose acetate succinate, hydroxypropyl methyl cellulose hexahydrophthalate, cellulose acetate phthalate, carboxymethyl ethyl cellulose and methacrylic acid copolymers.

* * * * *